United States Patent
Douglass et al.

[11] 3,953,590
[45] Apr. 27, 1976

[54] COMPOSITION AND METHOD FOR INHIBITING PERSPIRATION WITH S-SUBSTITUTED BENZOTHIOHYDROXIMIC ACID AND SALTS THEREOF

[75] Inventors: Miriam Lois Douglass, Bound Brook; Salvatore Joseph DeSalva, Somerset, both of N.J.

[73] Assignee: Colgate-Palmolive Company, New York, N.Y.

[22] Filed: Mar. 29, 1973

[21] Appl. No.: 346,068

Related U.S. Application Data

[62] Division of Ser. No. 107,476, Jan. 18, 1971, abandoned.

[52] U.S. Cl. .................................. 424/65
[51] Int. Cl.$^2$............................ A61K 7/32
[58] Field of Search ..................... 424/65

[56] References Cited
UNITED STATES PATENTS

| | | | |
|---|---|---|---|
| 2,786,865 | 3/1957 | Copenhaver | 260/453 |
| 3,374,260 | 3/1968 | Buchanan | 260/453 |

FOREIGN PATENTS OR APPLICATIONS

| | | | |
|---|---|---|---|
| 1,090,986 | 11/1967 | United Kingdom | 424/300 |

*Primary Examiner*—Dale R. Ore
*Attorney, Agent, or Firm*—Norman Blumenkopf; Murray M. Grill; Herbert S. Sylvester

[57] ABSTRACT

A method for inhibiting perspiration comprises applying to a site at which perspiration is normally exuded, an antiperspirant of the formula

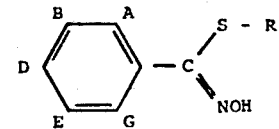

or a salt thereof. In preferred compounds, A, B, D, E, and G are hydrogen and R is phenyl, alkyl, hydroxyalkyl, aminoalkyl, alkenyl or oxopyridyl. Also useful are the corresponding hydrohalic acid salts. The compounds are preferably applied to the human axillae as aqueous antiperspirant compositions containing a surface active agent. Some of the S-substituted benzothiohydroximic acids and hydrohalic acid salts are new compounds of especially good antiperspirant activities, e.g., those in which the R group is linear alkyl of 6 to 9 carbon atoms, lower aminoalkyl, lower hydroxyalkyl, 1-oxopyridyl, and the hydrochloric acid salts of the compounds in which R is lower aminoalkyl.

12 Claims, No Drawings

COMPOSITION AND METHOD FOR INHIBITING PERSPIRATION WITH S-SUBSTITUTED BENZOTHIOHYDROXIMIC ACID AND SALTS THEREOF

This is a divisional of application Ser. No. 107,476, filed Jan. 18, 1971, now abandoned.

SUBJECT OF THE INVENTION:

This invention relates to a method for diminishing or preventing development of perspiration, especially in the axillae of the human body, by application to locations where perspiration is normally exuded, of S-substituted thiohydroximic acids or salts of amino derivatives thereof. Also within the invention are antiperspirant compositions comprising such active antiperspirant substances. Some of the antiperspirants employed are new compounds.

BACKGROUND OF THE INVENTION:

Present commercial antiperspirant compositions usually employ, as active ingredients, salts of aluminum or other metals which apparently act to promote hydration of skin protein, causing a swelling of the stratum corneum around the ostia of the sweat gland. Unfortunately, it seems that for the hydration and diminution of perspiration to be most extensive and effective, the antiperspirant metal salts must be applied at least once a day for about a week. It has been concluded that small amounts of such salts are absorbed by the skin but repeated applications are necessary for noticeably sufficient absorption to take place to diminish perspiration rates. Research has been undertaken to develop quicker acting antiperspirants which are more readily tolerated by the user and do not harm clothing materials. The present compounds, some of which are novel, have been found to achieve the desired results mentioned.

DESCRIPTION OF THE INVENTION

In accordance with the present invention a method for inhibiting perspiration comprises applying to a locus at which perspiration is normally exuded a perspiration-inhibiting S-substituted benzothiohydroximic acid of the formula:

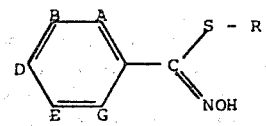

or a salt thereof, wherein R is selected from the group consisting of phenyl, alkyl, hydroxyalkyl, aminoalkyl, alkenyl, oxopyridyl, and substituted derivatives thereof, and A, B, D, E and G are individually selected from the group consisting of hydrogen, lower alkyl, lower alkoxy, lower aliphatic carboxylic, lower hydroxyalkyl, lower aminoalkyl, halogen, nitro, hydroxy, amino, and carboxyl, with the requirement that at least two of A, B, D, E and G are hydrogen. Another aspect of the invention is an antiperspirant composition which comprises from 0.0001 to 0.5% of a compound such as described above, in aqueous or nonaqueous media comprising from 0.5 to 50% of a surface active compound.

Of the compounds mentioned those which are considered to be novel and patentable as new compounds are those of the formula given wherein R is selected from the group consisting of normal alkyl of 6 to 9 carbon atoms, lower hydroxyalkyl, lower aminoalkyl, lower aminoalkyl hydrohalide, oxopyridyl and substituted derivatives thereof, and A, B, D, E and G are individually selected from the group consisting of hydrogen, lower alkyl, lower alkoxy, lower aliphatic carboxylic, lower hydroxyalkyl, lower aminoalkyl, halogen, nitro, hydroxy, amino, and carboxyl, with the requirement that at least two of A, B, D, E, and G are hydrogen. Preferably, R contains at least two carbon atoms.

DETALED DESCRIPTION OF THE INVENTION:

The S-substituted benzothiohydroximic acid compounds applied to normal sites of perspiration are preferably those wherein R is phenyl, alkyl, hydroxyalkyl, aminoalkyl, alkenyl or oxopyridyl, although derivatives of such substituted groups can be employed. Various non-interfering or helpful substituents on R include lower alkyl, lower alkoxy, lower hydroxyalkyl, lower aliphtic carboxylic, lower aminoalkyl, halogen, nitro, hydroxy, amino and carboxyl. The number of carbon atoms in a "lower" radical will generally be 1 to 7, preferably 1 to 6 and most preferably, 2 to 4. The number of substituents should be no more than three on an R group, preferably one, and most preferably, no substituent is present.

The number of carbon atoms in the various alkyl and alkenyl groups of the R substituents will generally be between 1 and 9, preferably 1 to 6 and most preferably, is from 2 to 4.

The substituents on the benzo portion of the present S-substituted benzothiohydroximic acids or salts, A, B, D, E and G, are non-intefering substituents which are independently selected from the group consisting of hydrogen, lower alkyl, lower alkoxy, lower aliphatic carboxylic acid, lower hydroxyalkyl lower aminoalkyl, halogen, nitro, hydroxy, amino and carboxyl but it is required that at least two of the group of A, B, D, E and G be hydrogen. The "lower" alkyl, alkoxy, aliphatic carboxylic, hydroxyalkyl, and aminoalkyl radicals will contain from 1 to 7 carbon atoms, preferably from 1 to 6 and most preferably, from 2 to 4. Also, it is preferred that four of A, B, D, E and G should be hydrogen and most preferably, the benzo group is unsubstituted.

The following table identifies various compounds which are useful in the practice of this invention. All are of the basic formula

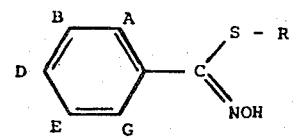

TABLE 1

| No. | A | B | D | E | G | R |
|-----|---|---|---|---|---|---|
| (1) | H | H | H | H | H | phenyl |
| (2) | H | H | H | H | H | (oxopyridyl) |
| (3) | H | H | H | H | H | n-hexyl |
| (4) | H | H | H | H | H | —CH₂CH₂OH |
| (5) | H | H | H | H | H | —CH₂CH₂NH₂.HCl |

TABLE 1-continued

| No. | A | B | D | E | G | R |
|---|---|---|---|---|---|---|
| (6) | H | H | H | H | H | —CH$_2$CH$_2$NH$_2$ |
| (7) | H | H | H | H | H | —CH$_2$CH$_2$N(CH$_3$)$_2$.HCl |
| (8) | H | H | H | H | H | —CH$_2$CH$_2$N(CH$_3$)$_2$ |
| (9) | Cl | H | Cl | H | Cl | phenyl |
| (10) | H | Cl | H | Cl | H | phenyl |
| (11) | H | H | Cl | H | H | p-chlorophenyl |
| (12) | H | H | NO$_2$ | H | H | p-nitrophenyl |
| (13) | H | H | Cl | H | H | o,o,p-trichlorophenyl |
| (14) | H | H | H | H | H | —CH$_2$CH$_2$CH=CH$_2$ |
| (15) | H | H | C$_2$H$_5$ | H | H | p-ethylphenyl |
| (16) | H | H | —CH$_2$COOH | H | H | —CH$_2$CH$_2$NO$_2$ |
| (17) | Br | H | Br | H | Br | —CH$_2$CH$_2$OC$_2$H$_5$ |
| (18) | H | H | H | H | H | -⟨phenyl⟩-CH$_2$COOH |
| (19) | H | H | COOH | H | H | -⟨phenyl⟩-CH$_2$CH$_2$OH |
| (20) | H | H | OH | H | H | -⟨phenyl⟩-OH |
| (21) | H | H | NH$_2$ | H | H | -⟨phenyl-NH$_2$⟩-OH |

Although the above-mentioned compounds produce antiperspirant effects when applied in accordance with this invention, many other compounds, in addition to those specifically exemplified, also possess such antiperspirant properties. For example, when substituents are changed from the indicated positions in Table 1 to other such positions illustrated, or are included in others of the indicated compounds, the compounds formed also have antiperspirant actions. When, within the limits given, the chain lengths of carbon contents of the various substituents are modified, useful products also result. When one substituent is replaced by another indicted substituent, the product produced will have antiperspirant action. Of course, the substituents employed will be those which are beneficial or innocuous, not those which chemically or otherwise unfavorably interact, either with the skin, chemicals on the skin, other positions of the active ingredient molecule or other components of the antipersirant composition.

Within the group of antiperspirant compounds described, are those which are novel and have especially good anhidrotic actions. Such compounds may be substituted in the same manner as described for the other antiperspirants, on the R and in the A, B, D, E and G positions. However, as with the previously described compounds, it is preferred that the R and benzo groups be unsubstituted. The new compounds are those, whether substituted or not, of the same basic formula previously given, with R being: an alkyl of 6 to 9 carbon atoms, preferably a normal alkyl, terminally joined to the sulfur atom; lower hydroxyalkyl; lower aminoalkyl; lower aminoalkyl hydrohalide, wherein the hydrohalide salt is of the amino of the lower aminoalkyl; or oxopyridyl.

The compounds disclosed can be made by various known methods, previously described with respect to some such compounds in 1. L. Cambi, Atti. acad. Lincei, 18, I, 687 (1909); Chem. Abstr., 4, 1738 (1910);
2. K. Nayata and S. Mizukami, Chem. Pharm. Bull. (Tokyo), 14 (11), 1263 (1966);
3. M. H. Benn, Can. J. Chem., 42, 2393 (1964); and
4. J. H. Davies, R. H. Davis, and P. Kirby, J. Chem. Soc., 431 (1938).

The first of these methods, illustrated in references (1) and (2), involves the monoalkylation of alkali metal salts of benzothiohydroximic acid with an alkyl halide.

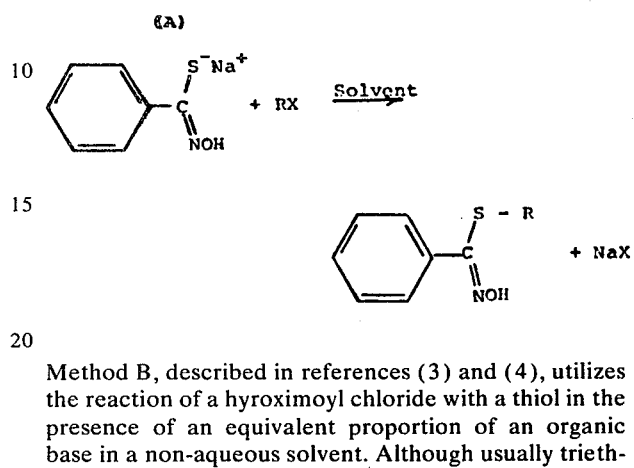

Method B, described in references (3) and (4), utilizes the reaction of a hyroximoyl chloride with a thiol in the presence of an equivalent proportion of an organic base in a non-aqueous solvent. Although usually triethylamine is employed as the base, sodium methoxide in methanol has also been used. In some instances, a thiolate, formed by reaction of a thiol with the base, is subsequently caused to react with hydroximoyl chloride. This method is exemplified in the following equation.

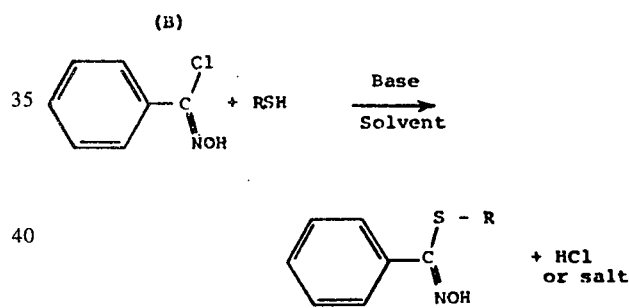

Method C, described in reference (4), depends on the formation of the thioimido ester from the reaction between a nitrile and a thiol in the presence of hydrogen chloride, with the imino group subsequently being replaced with a hydroxyimino.

Of the methods referred to above, that identified as (B) is preferred. The base employed will usually be triethylamine and the solvent will preferably be ethyl ether. The reaction may be effected at about room temperature or other suitable temperature, and at atmospheric pressure. Equimolar proportions of reagents are employed and the base used will be sufficient to react with and completely neutralize the hydrogen chloride generated. Of course, the choice of starting material, either the hydroximoyl chloride, the thiol or both, substituted or unsubstituted, will be obvious from the equations given, which are directed to the preparation of the unsubstituted compounds. When the salts of the aminoalkylbenzothiohydroximic acids are to be made, method (B) will usually be employed, since it might result directly in the production of the salt. Should it be desired to convert the hydrohalic acid salt to the amine, a molar proportion of neutralizing base may be added to the reaction product.

Most of the S-substituted benzothiohydroximic acids employed as antiperspirants in accordance with this invention are sufficiently water soluble or water-dispersible and subsequently useful, even if not in acid salt form, to produce aqueous or aqueous alcoholic solutions or other compositions of good antiperspirant activity. Because so little of the present compounds needs to be employed to have the desired antiperspirant effect, very dilute "solutions" can be used. For normal applications there will be applied to the surface from which perspiration would normally exude, from 1 microgram to 0.1 gram, preferably from 10 mcg. to 0.01 g. and more preferably, from 50 mcg. to 1 mg. When application is made to the human axillae, the amounts employed will be divided, half being applied to each axilla. Applications will be made daily or several times a day but care will generally be taken to avoid application of more than 0.1 g. per day and preferably the total amount applied will be less than 0.01 g./day. At such rates, the present materials are significantly safer than aluminum or other metal antiperspirant salts, which could tend to irritate the skin upon repeated use. Furthermore, they do not interfere with autonomic functions or produce systemic alterations therein, which is sometimes the case when excessive amounts of anticholinergic or tropine type drugs are used to prevent sweating.

For normal use as an antiperspirant, the very small amount of S-substituted benzothiohydroximic acid employed has essentially no effect on the base in which it is dispersed and therefore, that base may be of any of a wide variety of types of cosmetics, in any suitable form, so long as the ingredients thereof do not destroy or inhibit the activity of the S-substituted benzothiohydroximic acid or its salt. The antiperspirant cosmetic base may be in liquid, gel, cream, lotion, emulsion, solution, powder, dispersion, cake or solid form. It may be used as a liquid to be patted onto the surface to be treated, a liquid spray, an aerosol spray, a powder aerosol, roll-on, cream, "crayon" or a powder. Although such powder bases as talcs, diatomaceous earths, silica and bentonite may be used and non-aqueous or non-alcoholic media may be employed, e.g., fluorinated hydrocarbons, in pressure propelled products, aqueous, alcoholic or equivalent polar solvent solutions are preferred. These may include various adjuvant materials, such as emollients, e.g., stearic acid; thickeners, e.g., sodium carboxymethyl cellulose, polyvinyl alcohols, natural gums and inorganic silicates; emulsifying agents, e.g., sodium soaps of higher fatty acid; bactericides, e.g., hexachlorophene; supplementary solvents, e.g., glycerol; humectants, e.g., sorbitol; anti-foaming agents, e.g., silicones; hydrotropes, e.g., sodium toluene sulfonate; perfumes; and coloring agents, including dyes and pigments. Although it will usually be unnecessary to include additional antiperspirants, in some cases it may also be desired to employ metal salt antiperspirants and anticholinergic compounds, in combinations with the present antiperspirants, for additional effects. In such cases, the amounts of the supplementing antiperspirants may be diminished because of the presence of the materials of this invention. Of course, mixtures of the S-substituted benzothiohydroximic acids and salts thereof may also be used.

The antiperspirant compositions should contain from 0.0001 to 0.5% of S-substituted benzothiohydroximic acid or salt, preferbly from 0.001 to 0.05% and most preferbly from 0.002 to 0.02%. The compositions will usually be aqueous, alcoholic or aqueous alcoholic and the total content of such solvents may be from 10% to essentially 100%. Such content is 100% or essentially that when the only other ingredients are the S-substituted benzothiohydroximic acid or salt and a surface active agent. Preferably, the solvent content (water and alcohol) will be from 10 to 95% and usually will be from 20 to 80% of the composition. The major proportion of most compositions will be water, alcohol or a mixture thereof and generally the water will constitute a major proportion of any such solvent mixtures.

To improve the antiperspirant effects of the present compounds by enabling them better to contact the active sites from which perspiration is excreted it will be preferred to have present in these compositions sufficient quantity of surface active agent to improve the extent of contact with the skin or related surface. The surface active materials which may be used are preferably nonionic but anionic, cationic and amphoteric compounds are also useful. Such compounds are described at length in the text, Synthetic Detergents, Vol. II, by Schwartz, Perry and Berch, published in 1958 by Interscience Publishers, New York.

A preferred nonionic surface active agent is of the type sold under the tradename Pluronic, a condensation product of ethylene oxide with a hydrophobic base portion obtained by condensing propylene oxide with propylene glycol. Various Pluronics are suitable, including those identified as L61, L64 and F68, with the last mentioned being preferred. The molecular weights of such and similar condensation products of lower alkylene oxide with a lower alkylene oxide-lower alkylene glycol hydrophobic base are usually from about 2,000 to 20,000 and the lower alkylenes are of 2 to 4 carbon atoms, with those of three or four carbon atoms being used to make the hydrophobic portion of the molecule, which generally has molecular weight of from about 1,200 to 2,500, preferably 1,500 to 1,800.

Other nonionic surface active agents that are useful in the practice of the present invention include the condensation products of lower alkylene oxides, which are hydrophilic, with organic hydrophobes, either aliphtic or aromatic. Such compounds include detergents that are polyalkylene glycol esters, ethers or thioethers, wherein the hydrophobic portions of the molecules contain from about 8 to 18 carbon atoms and the number of alkylene oxides, almost always ethylene oxide, is from about 3 to 50. The hydrophobic groups may be long chain fatty alcohols or acids of 8 to 18 carbon atoms, or alkyl phenols or alkyl thiophenols in which the alkyl groups are of 6 to 12 carbon atoms, preferably of eight or nine carbon atoms, either straight chained or branched. Also useful are the tertiary trialkyl amine oxides wherein one alkyl has 10 to 18 carbon atoms and the other two are of 1 to 3 carbon atoms. Specific examples of such useful nonionic surface active agents include lauryl polyethoxy ethanol wherein there are present 20 moles of ethylene oxide per mole of fatty alcohol, nonyl phenol polyethoxyethanol having 15 moles of ethylene oxide per mole and dodecyl dimethylamine oxide.

In addition to or in replacement of the nonionic surface active agents, amphoteric compounds such as the alkyl beta-imino dipropionates, imidazoline compounds of the Miranol type and alkyl beta-amino propionates, the alkyl groups of which compounds are of 8 to 14 carbon atoms, are also useful. The cationic surface active agents are generally quaternary ammonium salts wherein one or two of the substituents on the quaternary nitrogen are hydrophobic "long chain" radicals and two or three are short chain alkyls, with the salt-forming ion being any suitable such ion, such as halide, including chloride, iodide and bromide, phosphate, nitrate, methosulfate, sulfate or sulfonate. Generally the hydrophobic substituents will contain from 8 to 25 carbon atoms, either as aliphatic or aliphaticaromatic radicals, e.g., alkyl or alkyl benzene. Specific examples of quaternary compounds are cetyl trimethyl ammonium bromide, benzethonium chloride, N-cetyl pyridinium bromide, and dodecyl dimethyl benzyl ammonium chloride.

Among the anionic surface active agents that are useful there may be mentioned the sulfated and sulfonated synthetic organic detergents, such as the higher alkyl sulfates; the higher alkyl aromatic sulfonates; the sulfonated amides of higher fatty acids; the higher fatty acid monoglyceride sulfates; the higher alkyl poly-lower alkoxy ether sulfates and sulfonates; the higher olefin sulfonates; and the mono- and di-higher alkyl sulfosuccinates. The salt-forming ions will preferably be sodium, potassium, ammonium or lower alkanolammonium. The alkyls will usually be of 8 to 18 carbon atoms and the lower alkoxies will be of 2 to 3 carbon atoms, preferably two carbon atoms. Specific examples of such materials which may be employed include: sodium lauryl sulfate; sodium n-octadecyl sulfate; monoethanolammonium pentadecyl sulfate; diethanolammonium oleyl sulfate; sodium dioctyl sulfosuccinate; sodium nonyl benzene sulfonate; potassium pentadecyl benzene sulfonate; sodium tridecyl benzene sulfonate; sodium salt of the lauric acid amide of taurine; sodium coconut oil monoglyceride sulfate; sodium N-lauroyl sarcoside; and the potassium salt of the oleic acid ester of isethionic acid. Also useful are the higher fatty acid soaps, such as those made from mixtures of coconut oil and tallow, saponified by sodium hydroxide or potassium hydroxide. Of course, some of these compounds may also be useful as emulsifiers in certain compositions within the invention.

Although wide ranges of contents of surface active agents may be employed, depending on the types of compositions being used, ordinarily the proportion of such surface active agent present will be from 1 to 25% and preferably will be from 2 to 10% of the composition. The proportions of adjuvants other than the solvents and the surface active agents will be from 0.1 to 75%, preferably from 1 to 25% and most preferably from 2 to 20% of the composition. Clearly, the contents of the various ingredients will, in part at least, depend on the types of products. For example, antiperspirant creams will contain much higher percentages of bases, such as stearic acid, than will solutions.

An advantage of the present composition is that the pH of the product is controllable. Thus, the pH of the water or other solvent system may be adjusted from that for distilled, deionized or tap water, to either an alkaline or acidic pH by the addition of buffering agents, e.g., sodium citrate, boric acid, disodium phosphate. Preferably, the pH will be maintained in the range from 5 to 10 and more preferably, from 6 to 8. At such pH's, skin irritation is minimized and damage to fabrics is usually prevented.

The amounts of the antiperspirant composition utilized will be controlled so that the desired content of the active antiperspirant compound(s) is within the ranges previously given. Also, the concentrations of such active ingredient will be correspondingly regulated. Normally, with respect to most cosmetics, the amount of composition applied will be from 0.1 to 5 grams, preferably from 0.5 to 2 grams. When liquids are used, the volumes employed will usually be from 0.1 to 5 ml., preferably from 0.2 to 2 ml. When application is to the human axillae, the amount employed will usually be distributed evenly between the axillae. Of course, the antiperspirants may be used on other parts of the human body which normally excrete perspiration, and, when desired, they may also be used on various animals.

The present antiperspirants are effective against natural animal and human perspiration and against that stimulated electrically or by pilocarpine injections. In fact, in comparative experiments it has been shown that the effectiveness of the present compounds against induced perspiration of certain animals, such as cats, is directly related to the effectiveness in vivo against natural human perspiration, induced by heat, humidity or tension.

The following examples illustrate various embodiments of the invention. These examples are not limitative of the invention. Unless otherwise indicated, all parts are by weight and all temperatures are in °C.

EXAMPLE 1

The compound S-(2-aminoethyl)benzothiohydroximic acid, hydrochloride salt, is made by reacting stoichiometric quantities of 2-aminoethanethiol hydrochloride, benzohydroximoyl chloride and sodium methoxide in an excess of absolute isopropyl alcohol. Reaction is at room temperature, 25°C., for a period of three hours, after which the desired product is obtained by evaporation of the solvent alcohol. Yield is 80%. The corresponding thiohydroximic acid is made by treating the hydrochloride salt with a stoichiometric quantity of base, e.g., sodium hydroxide. Yield for such conversion is 93% of that obtainable from the hydrohalide salt.

By the same method, using the corresponding starting materials, S-(2-dimethylaminoethyl)benzothiohydroximic acid hydrochloride and the corresponding benzothiohydroximic acid are made in yields of 28% and 42%, respectively.

The compounds described above are purified and melting points are taken. These are found to be 118°–119°C. (crystallization solvent being a mixture of methanol, ethyl acetate and diethyl ether); 128.3°–130.0°C. (crystallization solvent being ethyl acetate); -; and 58°–62°C. (decomposes), respectively. Analyses for carbon, hydrogen, nitrogen and sulfur, respectively, for the respective compounds are 45.98, 5.80, 11.87, 13.47; 52.87, 6.19, 14.04, 16.03; 50.24, 6.67, 10.53, 12.42; and 58.43, 7.41, 12.27, and 14.01.

The described compounds are also made by methods A and C, in the first of which, for example, S-(2-aminoethyl)benzothiohydroximic acid is made by reacting 2-aminoethyl chloride or bromide with the sodium salt of benzothiohydroxamic acid in the presence of ethanol, as a solvent. Stoichiometric quantities are employed at room temperature and the reaction takes about three hours. A similar reaction may be effected to produce S-(2-dimethylaminoethyl)benzothiohydroximic acid. The hydrohalide salts are made by reaction of a hydrohalic acid, such as HCl or HBr, with the hydroximic acid compound. Following method C, stoichiometric quantities of benzonitrile and 2-aminoethanethiol are reacted in the presence of an excess of hydrochloric acid in a suitable solvent, such as diethyl ether. The product is then reacted with hydroxylamine to convert it to the thiohydroximic acid. Such a reaction may also be undertaken with the dimethylaminoethanethiol starting material to product S-(2-dimethylaminoethyl)benzothiohydroximic acid hydrochloride. The hydrochloride salts then may be converted to the corresponding thiohydroximic acids by treatment with a stoichiometric quantity of base, e.g., sodium carbonate.

In addition to the specifically described reactions, other S-aminoalkylbenzothiohydroximic acids and hydrohalides are made by varying the starting materials so as to produce amino-lower alkyl substituents on the sulfur, as well as lower alkylamino-lower alkyl and di-lower alkylamino-lower alkyl substituents on the nitrogen on the sulfur. By such method, S-(2-aminobutyl)-benzothiohydroximic acid; S-(5-aminoamyl)benzothiohydroximic acid; S-(2-dipropylaminoethyl)benzothiohydroximic acid; and the corresponding hydrochlorides and hydrobromides are made. Also, similar compounds in which the benzo ring is substituted with one nitro, two methyls or three chlorines, at the D; A, G, and A, B, D positions respectively, can be made.

The S-(2-aminoethyl)benzothiohydroximic acid hydrochloride is tested for antiperspirant action, both in vivo, against human perspiration, and by the method of DeSalva et al. (Fed. Proc., 1969), utilizing the Cat Paw Assay method. In the latter method, both electrical and pilocarpine perspiration stimulations are used. In the human test, one milliliter of an aqueous solution of the hydroximic acid hydrochloride compound, containing 3% of dissolved Pluronic F68 is applied in equal portions to the axillae and continued applications are made daily for period of one week. A panel of four subjects is employed, pads are periodically utilized to absorb perspiration and the amount of absorbed moisture is weighed and compared with the average rate of excretion of perspiration before use of the experimental compound. The amount of the antiperspirant used in the aqueous solution is 200 micrograms, corresponding to a concentration of 0.02%. On the average, perspiration diminution is to significantly below that formerly obtaining.

In the Cat Paw Assay method of DeSalva et al., the average percentage change in perspiration rate varies from 18%, when 10 mcg. of the antiperspirant are employed, to 100% when 500 mcg. are used, with electrical stimulation. Using pilocarpine perspiration stimulation, 91% effectiveness is noted at an application rate as low as 10 mcg., and oddly, lesser effectivenesses are obtained at higher concentrations.

In addition to the reported results for S-(2-aminoethyl)-benzothiohydroximic acid hydrochloride, comparable effects are obtained when, instead of the hydrochloride, other acid salts, including the hydrohalides, e.g., hydrobromides, are used or when the acid form of the compound is employed. Similarly, when the previously described analogous compounds are utilized in the same applications, corresponding good antiperspirant activities result.

EXAMPLE 2

Following the procedure described in Example 1, S-phenyl-benzothiohydroximic acid is made (utilizing Method (B), purified and tested for anhidrotic effect. By the test method described in Example 1, it is found to be a useful antiperspirant in in vivo tests on humans at application rates beteen 10 and 500 micrograms per use. In such tests, perspiration diminishes to a level 50% or less than that previously observed without the use of such antiperspirant. When employed in combination with aluminum chlorhydroxide, with the concentration of the aluminum chlorhydroxide being 10% by weight of the solution used, and the concentration of the substituted benzothiohydroximate being from 0.001 to 0.05%, improvements in antiperspirant activity of the aluminum salt antiperspirant are obtained. Similarly, significant antiperspirant effects result when a mixture of 250 mcg. of S-phenylbenzothiohydroximic acid and 250 mcg. of S-(2-aminoethyl)-benzothiohydroximic acid are utilized from a similar aqueous solution. Such antiperspirant effects are also obtainable when the proportion of alcohol in the composition applied is from 10 to 40% thereof, with water being present in greater proportion. Also, when the surface active agent employed is benzethonium chloride, sodium coconut oil fatty acids monoglyceride sulfate, potassium lauryl alcohol sulfate, sodium linear pentadecyl benzene sulfonate or dodecyl beta-imino dipropionate, the anhidrotic activity of the benzothiohydroximic acid is improved over that when such a surface active compound is not present. Yet, even in the absence of the surface active compound, appreciable anhidrotic activity is obtained.

Although test results on humans are very significant, they are necessarily less accurate and less reproducible than results obtained by the DeSalva et al. method, mentioned above. Following that method, utilizing electrical stimulation of perspiration, a complete reduction in perspiration to 0% is obtained when 500 mcg. of S-phenylbenzothiohydroximic acid are used and measurable reductions are obtained when the amount employed is decreased down to one mcg. When sweating is stimulated by pilocarpine, 100% reduction is obtained at 500 mcg., 100 mcg. and 50 mcg. applications, with approximately 50% reduction at 10 mcg. and measurable reduction often obtained at one mcg.

EXAMPLE 3

The compounds S-n-hexylbenzothiohydroximic acid and S-n-dodecylbenzothiohydroximic acid are made by Method (B), as described in Example 1, purified, analyzed and tested for antipersiprant activity. The hexyl-substituted compound is a colorless liquid and the dodecyl-substituted compound, crystallized from diethyl ether, is a solid with a melting point in the range 52.5°–54.5°C. The carbon, hydrogen, nitrogen and sulfur analyses of these compounds are, respectively, 65.26, 8.54, 6.10, 13.41; and 71.64, 9.63, 4.11 and 9.82%.

Perspiration inhibition tests on humans show S-n-hexylbenzothiohydroximic acid to be effective at application rates of 200–500 mcg., even from pure water solutions. Using the DeSalva et al. method, 100% effectiveness is obtained against electrically stimulated sweating at 500 mcg. and about 60% effectiveness is obtained at the same concentration when sweating is induced by pilocarpine. At decreased rates, corresponding to 100 mcg., a 50% reduction against pilocarpine-induced sweating is noted, whereas the reduction against electrically stimulated sweating is less. Using such test methods, the S-n-dodecyl benzothiohydroximic acid is found to be substantially inactive.

EXAMPLE 4

Following Method (B), as described in Example 1, S-(2-hydroxyethyl)benzothiohydroximic acid is made, purified and tested. This compound, crystallized from chloroform, has a melting point of 97.4°–98.0°C. and analyzes 54.63% carbon, 5.73% hydrogen, 7.21% nitrogen and 16.13% sulfur. When tested for anhidrotic effects in vivo, it is found to have a substantial activity, by the test of Example 1. Utilizing the DeSalva et al. method, it diminishes perspiration by over 50% at 500 mcg. application rate and in some instances the diminution is approximately 90%. Similarly, the analogous compounds, in which ethyl is replaced with isopropyl or n-butyl, are useful anhidrotic agents.

EXAMPLE 5

S-Carboxymethyl benzothiohydroximic acid is made by the method of Example 1, according to equation (B), crystallized from water, analyzed and tested. It has a melting point of 123°–125°C. and analyzes 50.82% carbon, 4.60% hydrogen, 6.41% nitrogen and 14.98% sulfur. It and other ower aliphatic carboxylic acid analogues are useful anhidrotic materials for diminishing animal and human perspiration, when applied to normal sites thereof at the rate of 500 mcg. per application.

EXAMPLE 6

S-[2-(1-Oxopyridyl)]benzothiohydroximic acid is made according to the method of Example 1, (B) equation, utilizing the indicated starting materials. After purification from chloroform, it is found that the melting point (product decomposes) is 121°–125°C. It contains 58.01% carbon, 4.36% hydrogen, 11.17% nitrogen and 12.86% sulfur, according to analysis. When tested according to the method of Example 1, it inhibits human perspiration effectively, usually diminishing it to less than 50% of normal at application rates of 500 mcg. In tests according to the method of De Salva et al., such diminution is complete against pilocarpine-induced perspiration but is not noted when perspiration is induced electrically, at the 500 mcg. application rates.

The compounds and compositions described in the above examples and in the specification are cosmetically acceptable, being compatible with cosmetic ingredients, sufficiently stable on storage and not harmful to the user thereof. They do not cause allergic reactions nor do they interfere with body functions. Also, their "neutral" pH, generally from 6 to 9, does not irritate the skin, even in the recently shaved axillae.

The invention has been described with respect to specific descriptions, examples and illustrations thereof but is not to be limited to these inasmuch as it is clear to one of skill in the art, with the present disclosure before him, that various modifications may be made and equivalents substituted without going beyond the scope of the invention.

What is claimed is:

1. A method for inhibiting perspiration which comprises applying to the active sites from which perspiration is excreted one microgram to 0.1 gram of a perspiration-inhibiting S-substituted benzothiohydroximic acid of the formula:

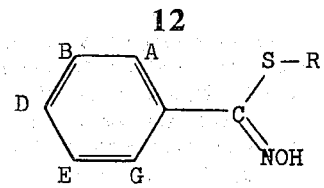

or a hydrohalic acid salt thereof, wherein R is selected from the group consisting of phenyl, $C_1$-$C_9$ alkyl, $C_1$-$C_9$ hydroxyalkyl, $C_1$-$C_9$ aminoalkyl, $C_1$-$C_9$ alkenyl, oxopyridyl, and substituted derivatives thereof, wherein the substituents on R are limited to three in number and are selected from the group consisting of $C_1$-$C_7$ alkyl, $C_1$-$C_7$ alkoxy, $C_1$-$C_7$ hydroxyalkyl, $C_1$-$C_7$ aliphatic carboxylic, $C_1$-$C_7$ amino-alkyl, halogen, nitro, hydroxy, amino and carboxyl and A, B, D, E and G are individually selected from the group consisting of hydrogen, $C_1$-$C_7$ alkyl, $C_1$-$C_7$ alkoxy, $C_1$-$C_7$ aliphatic carboxylic, $C_1$-$C_7$ hydroxyalkyl, $C_1$-$C_7$ aminoalkyl, halogen, nitro, hydroxy, amino, and carboxyl, with the requirement that at least two of A, B, D, E and G are hydrogen.

2. A method according to claim 1 wherein R is either monosubstituted or unsubstituted and at least four of A, B, D, E and G are hydrogens.

3. A method according to claim 2 wherein R is unsubstituted, the alkyl and alkenyl groups are of 6 to 9 carbon atoms, and each of A, B, D, E and G is hydrogen.

4. A method according to claim 1 wherein an effective perspiration-inhibiting quantity of the S-substituted benzothiohydroximic acid or salt thereof is employed, within the range of 1 microgram to 0.1 gram, in water and application is to human axillae.

5. A method according to claim 3 wherein an effective perspiration-inhibiting quantity of the S-substituted benzothiohydroximic acid or salt thereof is employed, within the range of 1 microgram to 0.1 gram, in water and application is to human axillae.

6. A method according to claim 5 wherein the perspiration-inhibiting compound applied is S-phenylbenzothiohydroximic acid.

7. A method according to claim 5 wherein the perspiration-inhibiting compound applied is S-[2-(1-oxopyridyl)]benzothiohydroximic acid.

8. A method according to claim 5 wherein the perspiration-inhibiting compound applied is S-n-hexylbenzothiohydroximic acid.

9. A method according to claim 5 wherein the perspiration-inhibiting compound applied is S-(2-hydroxyethyl)benzothiohydroximic acid.

10. A method according to claim 5 wherein the perspiration-inhibiting compound applied is S-(2-aminoethyl)benzothiohydroximic acid hydrochloride.

11. An antiperspirant composition which comprises from about 0.0001 to 0.5% of a perspiration-inhibiting S-substituted benzothiohydroximic acid of the formula:

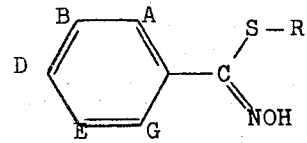

or a hydrohalic acid salt thereof, wherein R is selected from the group consisting of phenyl, $C_1$-$C_9$ alkyl, $C_1$-$C_9$ hydroxyalkyl, $C_1$-$C_9$ aminoalkyl, $C_1$-$C_9$ alkenyl, oxopyridyl, and substituted derivatives thereof, wherein the substituents on R are limited to three in number and are selected from the group consisting of $C_1$–$C_7$ alkyl, $C_1$–$C_7$ alkoxy, $C_1$–$C_7$ hydroxyalkyl, $C_1$–$C_7$ aliphatic carboxylic, $C_1$–$C_7$ aminoalkyl, halogen, nitro, hydroxy, amino and carboxyl and A, B, D, E and G are individually selected from the group consisting of hydrogen, $C_1$–$C_7$ alkyl, $C_1$–$C_7$ alkoxy, $C_1$–$C_7$ aliphatic carboxylic, $C_1$–$C_7$ hydroxyalkyl, $C_1$–$C_7$ aminoalkyl, halogen, nitro, hydroxy, amino, and carboxyl, with the requirement that at least two of A, B, D, E and G are hydrogen, from about 0.5 to 50% of a surface active agent selected from the group consisting of nonionic, anionic, cationic and amphoteric surface active compounds, and from about 10% to essentially 100% of a member selected from the group consisting of water, alcohol and water-alcohol mixtures.

12. A composition according to claim 11 in which A, B. D, E and G are each hydrogen, the alkyls of R are of 6 to 9 carbon atoms, and R is unsubstituted.

* * * * *